United States Patent [19]

Braisted et al.

[11] Patent Number: 5,081,118
[45] Date of Patent: Jan. 14, 1992

[54] BENZOTHIAZINE DIOXIDE DERIVATIVES

[75] Inventors: Andrew C. Braisted, Berkeley, Calif.; Philip D. Hammen, East Haddam, Conn.

[73] Assignee: Pfizer Inc., New York, N.Y.

[21] Appl. No.: 460,121

[22] PCT Filed: Oct. 26, 1987

[86] PCT No.: PCT/US87/02783
§ 371 Date: Apr. 26, 1990
§ 102(e) Date: Apr. 26, 1990

[87] PCT Pub. No.: WO89/03682
PCT Pub. Date: May 5, 1989

[51] Int. Cl.$^5$ .............. C07D 279/02; A61K 31/54
[52] U.S. Cl. .................. 514/226.5; 544/49
[58] Field of Search ............. 544/49; 514/226.5

[56] References Cited

U.S. PATENT DOCUMENTS

| | | | |
|---|---|---|---|
| 3,591,584 | 7/1971 | Lombardino | 544/49 |
| 3,892,740 | 7/1975 | Lombardino | 544/49 |
| 4,551,452 | 11/1985 | Marfat | 514/222 |
| 4,599,406 | 7/1986 | Bruzzese et al. | 544/49 |
| 4,829,062 | 5/1989 | Lombardino et al. | 514/226.5 |

Primary Examiner—Catherine S. Kilby Scalzo
Attorney, Agent, or Firm—Peter C. Richardson; Paul H. Ginsburg

[57] ABSTRACT

A series of novel oxyethyl derivatives of certain selected enolic oxicam compounds are disclosed, including certain novel oxyethyl derivatives of 4-hydroxy-2-methyl-N-(2-pyridinyl)-2H-1,2-benzothiazine-3-carboxamide 1,1-dioxide (piroxicam). These particular compounds are useful in therapy as prodrug forms of the known anti-inflammatory and analgesic oxicams. Said oxyethyl derivatives of enolic oxicam compounds like piroxicam are of the formulae:

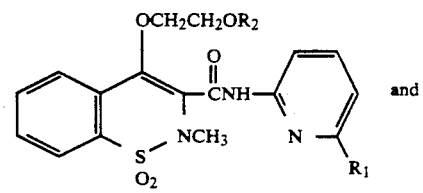

I

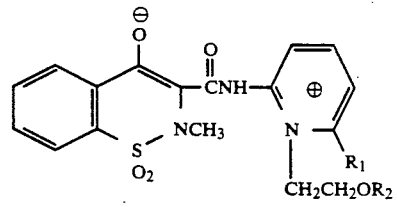

II wherein $R_1$ is hydrogen, methyl, fluorine or chlorine, and $R_2$ is hydrogen or —$COOR_3$ wherein $R_3$ is alkyl having from one to eight carbon atoms.

10 Claims, No Drawings

BENZOTHIAZINE DIOXIDE DERIVATIVES

TECHNICAL FIELD

This invention relates to new and useful benzothiazine dioxide derivatives. More particularly, it is concerned with certain novel oxyethyl derivatives of 4-hydroxy-2-methyl-N-(2-pyridinyl)-2H-1,2-benzothiazine-3-carboxamide 1,1-dioxide and several other closely-related oxicams, which are of especial value as prodrugs in view of their chemotherapeutic properties.

BACKGROUND ART

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including piroxicam. The latter substance is a member of a class of anti-inflammatory/analgesic N-heteroaryl-4-hydroxy-2-methyl-2H-1,2-benzothiazine-3-carboxamide 1,1-dioxides (known as oxicams) described and claimed in U.S. Pat. No. 3,591,584 and is specifically, 4-hydroxy-2-methyl-N-(2-pyridinyl)-2H-1,2-benzothiazine-3-carboxamide 1,1-dioxide. Other agents of this type are disclosed in U.S. Pat. Nos. 3,787,324, 3,822,258, 4,180,662 and 4,376,768, as well as in German Offenlegungsschrift No. 2,756,113 and Published European Patent Application No. 138,223. In U.S. Pat. No. 4,434,164, there are specifically described and claimed the ethylenediamine, monoethanolamine and diethanolamine salts of 4-hydroxy-2-methyl-N-(2-pyridinyl)-2H-1,2-benzothiazine-3-carboxamide 1,1-dioxide, which are particularly valuable in pharmaceutical dosage forms as non-steroidal therapeutic agents for the treatment of painful inflammatory conditions, such as those caused by rheumatoid arthritis, since they are all crystalline, non-hygroscopic, rapidly-dissolving solids with high water solubility. In U.S. Pat. No. 4,309,427, there are disclosed certain novel acyl derivatives (i.e., enol esters) of 4-hydroxy-2-methyl-N-(2-pyridinyl)-2H-1,2-benzothiazine-3-carboxamide 1,1-dioxide and 4-hydroxy-2-methyl-N-(6-methyl-2-pyridinyl)-2H-1,2-benzothiazine-3-carboxamide 1,1-dioxide, which are useful as non-steroidal therapeutic agents for alleviating various inflammatory conditions, including those of the skin, especially when given by the topical route of administration. However, in the continuing search for still more improved anti-inflammatory/analgesic agents, there is a need for anti-arthritic agents that are orally administrable.

In this connection, it is to be noted that while the prior described enolic oxicam lower alkyl ethers of U.S. Pat. No. 3,892,740 do not possess anti-inflammatory activity to any substantial degree, the more recently described anti-inflammatory oxyalkyl ethers of the enolic oxicams of U.S. Pat. No. 4,551,452 all require that the oxyalkyl moiety be restricted to —CH$_2$—O—, —CH(CH$_3$)—O— or —CH(C$_6$H$_5$)—O—. As a result, there is little or no information available about the effect of other oxyalkyl ethers in this area and particularly, about compounds like the corresponding enolic oxicam lower oxyalkyl ethers wherein the alkyl moiety is exclusively arranged in a straight chain.

DISCLOSURE OF THE INVENTION

In accordance with the present invention, it has now been found that certain novel oxyethyl derivatives of 4-hydroxy-2-methyl-N-(2-pyridinyl)-2H-1,2-benzothiazine-3-carboxamide 1,1-dioxide and several other closely-related known oxicams are useful in therapy as prodrug forms of the known anti-inflammatory and analgesic oxicams. Consequently, the compounds of this invention are useful in therapy as non-steroidal therapeutic agents for alleviating painful inflammatory conditions such as those caused by rheumatoid arthritis, for example. The novel compounds of this invention are of the formula:

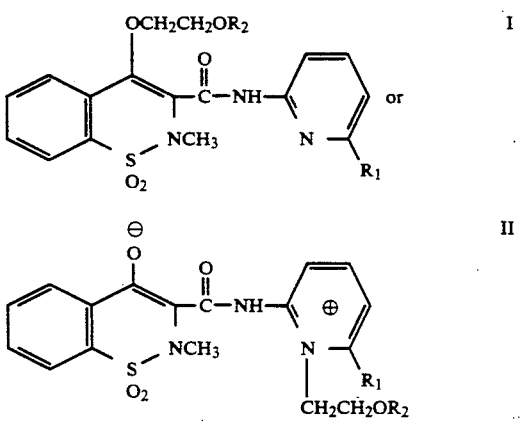

wherein R$_1$ is hydrogen, methyl, fluorine or chlorine, and R$_2$ is hydrogen or —COOR$_3$ wherein R$_3$ is alkyl having from one to eight carbon atoms.

The compounds of this invention are useful in therapy as prodrug forms of the known anti-inflammatory and analgesic oxicams from which they are derived. The term "prodrug", when used in this connection, refers to compounds which are drug precursors, which following administration and absorption in the body release the drug in vivo by some metabolic pathway or process such as hydrolysis. Accordingly, these novel compounds are particularly valuable as non-steroidal therapeutic agents for the treatment of painful inflammatory conditions, especially those caused by rheumatoid arthritis, and are particularly adapted for use in various pharmaceutical dosage forms, including those designed for oral, topical or parenteral administration. Moreover, the prodrugs of this invention are unusual in that they exhibit anti-inflammatory activity to a high degree in contrast to the enolic oxicam lower alkyl ethers of the aforesaid prior art (U.S. Pat. No. 3,892,740). They also exhibit good oral absorption, as compared to the parent acidic oxicams from which they are derived. Accordingly, the preferred method of administration for the presently-claimed compounds is oral, although parenteral and topical formulations are also readily made available with these compounds and such formulations are found to be useful.

Of especial interest in this connection are the preferred compounds of the invention where R$_1$ in the structural formula is hydrogen (i.e., derivatives of piroxicam), and R$_2$ is hydrogen or —COOR$_3$ wherein R$_3$ is alkyl having from one to eight carbon atoms. Typical and preferred member compounds of the invention include 4-(2-hydroxyethyloxy)-2-methyl-N-(2-pyridinyl)-2H-1,2-benzothiazine-3-carboxamide 1,1- dioxide, 4-(2-hydroxyethyloxy)-2-methyl-N-(6-methyl-2-pyridinyl)-2H-1,2-benzothiazine-3-carboxamide 1,1-dioxide and N-[1-(2-hydroxyethyl)-2-pyridinium]-2-methyl-2H-1,2-benzothiazine-3-carboxamide 1,1-dioxide 4-enolate. These particular compounds are especially effective in treating many painful inflammatory conditions by the oral route of administration.

DETAILED DESCRIPTION

In the process for preparing the novel compounds of the invention, the parent oxicam compound of the formula:

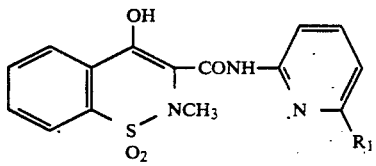

wherein $R_1$ is defined as aforesaid, is treated with at least an equivalent amount in moles of an oxyethyl halide of the formula:

$XCH_2CH_2OR_2$ wherein $R_2$ is as previously defined and X is either chlorine, bromine or iodine. This reaction is normally carried out in a reaction-inert organic solvent, preferably under substantially anhydrous conditions, in the presence of at least an equivalent amount of an appropriate standard base (e.g., triethanolamine or potassium carbonate). A particularly convenient reaction system employs acetone as the solvent and potassium carbonate as the base, with up to three or more equivalents of sodium iodide added, if desired, when the oxyethyl halide employed is other than an iodide, in order to enhance the rate of the reaction. It should be noted that the amount of standard base employed must be such that it is present in sufficient amount to neutralize the liberated hydrogen halide formed in the reaction. Excess of the reagent $R_2OCH_2CH_2X$ is not critical to the reaction, but such excess will generally be used in order to shift the reaction to completion in a shorter period of time. The rate of reaction will also depend greatly on the nature of X (e.g., I>Br>Cl) and to some extent on the nature of the $R_2OCH_2CH_2$— group (where $R_2$ is hydrogen or an organic radical as previously defined). In general, the reaction is conducted at a temperature of from about 50° C. up to about 100° C. for a period of at least about 24 hours and preferably for a period of about five to about seven days. When acetone is employed as the solvent and potassium carbonate as the base, the reflux temperature of acetone is a particularly convenient reaction temperature for these purposes. The reaction is most conveniently followed by high pressure liquid chromatography, thereby determining reaction times sufficient to provide complete reaction and at the same time, avoiding any unnecessary heating and excessive reaction times which can increase the level of by-product formation and reduce yields. Upon completion of the reaction, the desired oxyethyl derivatives are readily recovered in a conventional manner and preferably by using known chromatographic techniques.

The starting materials required for preparing the novel oxyethyl derivatives of this invention are all known compounds. For instance, 4-hydroxy-2-methyl-N-(2-pyridinyl)-2H-1,2-benzothiazine-3-carboxamide 1,1-dioxide (piroxicam) and 4-hydroxy-2-methyl-N-(6-methyl-2-pyridinyl)-2H-1,2-benzothiazine-3-carboxamide 1,1-dioxide are both fully described in U.S. Pat. No. 3,591,584 to J. G. Lombardino, as well as in the paper by J. G. Lombardino et al., appearing in the *Journal of Medicinal Chemistry*, Vol. 16, p. 493 (1973), including their synthesis from readily available organic compounds. The other closely-related oxicams required as starting materials in the process of this invention are readily available by methods well known to those skilled in the art, e.g., see the patent references to the other oxicams cited in the background section of the instant specification.

The oxicam prodrugs of the present invention are all readily adapted to therapeutic use as anti-inflammatory agents. For instance, 4-(2-hydroxyethyloxy-2-methyl-4-(2-pyridinyl)-2H-1,2-benzothiazine-3-carboxamide 1,1-dioxide, a typical and preferred agent of the present invention, exhibits anti-inflammatory activity in the standard carrageenin-induced rat foot edema test [described by C. A. Winter et al., *Proc. Soc. Exp. Biol. Med.*, Vol. 111, p. 544 (1962)], where it was found to cause a 48% inhibition in swelling at the 32 mg./kg. dose level when given by the oral route. The herein described derivatives exhibit additional advantages. For instance, they all exhbit good oral absorption as compared to the parent oxicam from which they are derived. In this connection, it is to be noted that the aforesaid preferred agent of the present invention exhibits a rather surprisingly high oral absorption potential (e.g., a value of 1.81) when tested orally at 22.7 mg. according to the standard test procedure described by J. B. Dressman et al., as set forth in the *Journal of Pharmaceutical Sciences*, Vol. 74, No. 5, p. 588 (1985).

The herein described oxicam prodrugs of this invention can be administered via either the oral, parenteral or topical routes. In general, these compounds are most desirably administered in doses ranging from about 5.0 mg. up to about 1000 mg. per day, although variations will necessarily occur depending upon the weight and condition of the subject being treated and the particular route of administration chosen. However, a dosage level that is in the range of from about 0.08 mg. to about 16 mg. per kg. of body weight per day is most desirably employed. Nevertheless, variations may still occur depending upon the individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing harmful side effects provided that such higher dose levels are first divided into several small doses for administration throughout the day.

The oxicam prodrugs of this invention may be administered alone or in combination with pharmaceutically acceptable carriers by either of the three routes previously indicated. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these oxicam prodrugs in either sesame or peanut oil or in aqueous propylene glycol may be employed. The aqueous solutions should be suitably buffered (pH > 8) if necessary and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid oxicam oxyethyl derivatives topically when treating inflammatory conditions of the skin or eye and this may be preferably done by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150-190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg./kg., via the oral route of administration.

PREPARATION A

To a well-stirred solution consisting of 17.89 g. (0.104 mole) 2-iodoethanol dissolved in 25 ml. of benzene, there is added in a dropwise manner a solution consisting of 8 ml. (0.104 mole) of methyl chloroformate in 25 ml. of benzene. The reaction mixture is then cooled to 0° C. with the aid of an ice/water bath, at which point a solution consisting of 8.3 ml. (0.104 mole) of pyridine dissolved in 25 ml. of benzene is slowly added thereto. The resulting reaction mixture is then stirred for one hour at 0° C. and for four hours at room temperature (~20° C.) while under a nitrogen atmosphere. At the end of this time, 100 ml. of diethyl ether is added to the mixture and the precipitated pyridine hydriodide which forms is then removed from the system by means of suction filtration. The filtrate is then washed twice with 3N hydrochloric and once with brine, followed by drying over anhydrous sodium sulfate. After removal of the drying agent by means of filtration and the solvent by means of evaporation under reduced pressure, there is obtained 2-iodoethyl methyl carbonate as the residual material.

PREPARATION B

To a well-stirred solution consisting of 34.40 g. (0.20 mole) of 2-iodoethanol dissolved in 25 ml. of benzene precooled to 0° C. with the aid of an ice/water bath, there is added in a dropwise manner a solution consisting of 19.1 ml. (0.20 mole) of ethyl chloroformate dissolved in 25 ml. of benzene. Upon completion of this step, the reaction mixture is treated with 19.1 ml. (0.20 mole) of pyridine which is also added in a dropwise manner. The resulting suspension is then stirred for a period of one hour at 0° C. (while under a nitrogen atmosphere) and for six hours at room temperature (~20° C.). At the end of this time, the pyridine hydriodide is removed by filtration and the organic filtrate is washed twice with 50 ml. of 3N hydrochloric acid and once with 50 ml. of brine, followed by drying over anhydrous magnesium sulfate. After removal of the drying agent by means of filtration and the solvent by means of evaporation under reduced pressure, there is obtained 2-iodoethyl ethyl carbonate as the residual material.

PREPARATION C

To a well-stirred solution consisting of 17.89 g. (0.104 mole) of 2-iodoethanol dissolved in 25 ml. of benzene precooled to 0° C. with the aid of an ice/water bath, there is added in a dropwise manner a solution consisting of 20 g. (0.104 mole) n-octyl chloroformate dissolved in 25 ml of benzene. Upon completion of this step, the reaction mixture is treated with 8.3 ml (0.104 ml.) of pyridine which is also added in a dropwise manner. The resulting suspension is then stirred for 30 minutes at 0° C. and thereafter for a period of five hours at room temperature while under a nitrogen atmosphere. At the end of this time, 100 ml. of diethyl ether is added to the mixture and the precipitated pyridine hydriodide is then removed by filtration. The organic filtrate is thereafter washed twice with 3N hydrochloric acid and once with brine, followed by drying over anhydrous magnesium sulfate. After removal of the drying agent by means of filtration and the solvent by means of evaporation under reduced pressure, there is obtained 2-iodoethyl n-octyl carbonate as the residual material.

EXAMPLE 1

A. In a 1000 ml. four-necked, round-bottomed reaction flask equipped with mechanical stirrer and reflux condenser, there was placed a well-stirred mixture consisting of 32.1 g. (0.096 mole) of 4-hydroxy-2-methyl-N-(2-pyridinyl)-2H-1,2-benzothiazine-3-carboxamide 1,1- dioxide, 100 g. (0.58 mole) of 2-iodoethanol and 26.5 g. (0.192 mole) of anhydrous potassium carbonate in 600 ml. of acetone. The resulting reaction mixture was then refluxed for a period of approximately seven days, cooled to room temperature (~20° C.) and filtered. The organic filtrate was subsequently concentrated in vacuo to remove the solvent, and the residual material was thereafter triturated with 400 ml. of ethyl acetate and then washed with 300 ml. of water. The yellow crystals (yield, 2.6 g.) which formed on the addition of water to the organics were subsequently collected by means of suction filtration and later added to the crystals (yield, 1.46 g.) which formed on allowing the residue to stand overnight (~16 hours) at room temperature. The combined yield of N-[1-(2-hydroxyethyl)-2-pyridinium]-2-methyl-2H-1,2-benzothiazine-3-carboxamide 1,1-dioxide 4-enolate (m.p. 207°-208° C.) obtained in this manner amounted to 4.06 g. (crop A).

B. The remaining residue, obtained after removal of the crystals as described above, was then chromatographed on a column of silica gel (120 g.), using ethyl acetate as the eluant, and like fractions were subsequently crystallized from diethyl ether to give 8.8 g. of pure 4-(2-hydroxyethyloxy)-2-methyl-N-(2-pyridinyl)-2H-1,2-benzothiazine-3-carboxamide 1,1-dioxide (m.p. 131°-134° C.) in the form of pale yellow crystals. An additional 1.4 g. of product was obtained from the mother liquor to bring the total yield to 10.2 g. (28%). The pure product was further characterized by means of nuclear magnetic resonance data, mass spectroscopy and high pressure liquid chromatography (HPLC), in addition to elemental analysis.

Anal. Calcd. for $C_{17}H_{17}N_3O_5S$: C,54.39; H,4.56; N,11.19. Found: C, 54.51; H,4.32; N, 11.08.

C. Later fractions, obtained during the above chromatographic step, gave 700 mg. of pure N-[1-(2-hydroxyethyl)-2-pyridinium]-2-methyl-2H-1,2-benzothiazine-3-carboxamide 1,1-dioxide 4-enolate (m.p. 218°-220° C.) in the form of yellow crystals (crop B). This material was combined with the crystalline product obtained before the chromatographic step (viz., 4.06 g. of crop A), so the combined yield of crop A and crop B amounted to 4.76 g. The latter material was then slurried with fresh hexane to ultimately afford 4.72 g. (15%) of pure N-[1-(2-hydroxyethyl)-2-pyridinium]-2-methyl-2H-1,2-benzothiazine-3-carboxamide 1,1-dioxide 4-enolate (m.p. 207°-208° C.). The pure product was further characterized by means of nuclear magnetic resonance data and high pressure liquid chromatography (HPLC). A sample for elemental analysis was prepared by recrystallizing the product from dimethylacetamide/methanol.

Anal. Calcd. for $C_{17}H_{17}N_3O_5S$, corrected for 1.63% inorganics: C,53.50; H,4.48; N,11.01. Found: C, 53.81; H, 4.44; N, 11.05.

EXAMPLE 2

The procedure described in Example 1 is repeated except that 2-iodoethyl methyl carbonate (the product of Preparation A) is the oxyethyl halide reagent of choice employed instead of 2-iodoethanol, using the same molar proportions as before. In this particular case, the corresponding final products obtained are 4-[2-(methoxycarbonyloxy)ethyloxy]-2-methyl-N-(2-pyridinyl)-2H-1,2-benzothiazine-3-carboxamide 1,1-dioxide and N-{1-[2-(methoxycarbonyloxy)ethyl]-2-pyridinium}-2-methyl-2H-1,2-benzothiazine-3-carboxamide 1,1-dioxide 4-enolate, respectively.

EXAMPLE 3

The procedure described in Example 1 is repeated except that 2-iodoethyl ethyl carbonate (the product of Preparation B) is the oxyethyl halide reagent of choice employed instead of 2-iodoethanol, using the same molar proportions as before. In this particular case, the corresponding final products obtained are 4-[2-(ethoxycarbonyloxy)ethyloxy]-2-methyl-N-(2-pyridinyl)-2H-1,2-benzothiazine-3-carboxamide 1,1-dioxide and N-{1-[2-(ethoxycarbonyloxy)ethyl]-2-pyridinium}-2-methyl-2H-1,2-benzothiazine-3-carboxamide 1,1-dioxide 4-enolate, respectively.

EXAMPLE 4

The procedure described in Example 1 is repeated except that 2-iodoethyl n-octyl carbonate (the product of Preparation C) is the oxyethyl halide reagent of choice employed instead of 2-iodoethanol, using the same molar proportions as before. In this particular case, the corresponding final products obtained are 2-methyl-4-[2-(n-octyloxycarbonyloxy)ethyloxy]-N-(2-pyridinyl)-2H-1,2-benzothiazine-3-carboxamide 1,1-dioxide and N-{1-[2-(n-octyloxycarbonyloxy)ethyl]-2-pyridinium}-2-methyl-2H-1,2-benzothiazine-3-carboxamide 1,1-dioxide 4-enolate, respectively.

EXAMPLE 5

The procedure described in Example 1 was essentially followed except that 4-hydroxy-2-methyl-N-(6-methyl-2-pyridinyl)-2H-1,2-benzothiazine-3-carboxamide 1,1-dioxide (prepared as described in U.S. Pat. No. 3,591,584) was the starting material employed in place of 4-hydroxy-2-methyl-N-(2-pyridinyl)-2H-1,2-benzothiazine-3-carboxamide 1,1-dioxide, using the same molar proportions as before. In this particular case, the only corresponding final product actually isolated was 4-(2-hydroxyethyloxy)-2-methyl-N-(6-methyl-2-pyridinyl)-2H-1,2-benzothiazine-3-carboxamide 1,1-dioxide (m.p. 180°-182° C.). The yield of pure product amounted to 75% of the theoretical value.

Anal. Calcd. for $C_{18}H_{19}N_3O_5S$: C,55.52; H,4.56; N,10.79. Found: C,55.31; H,4.82; N,10.68.

EXAMPLE 6

The following oxyethyl oxicam final products of Examples 1B, 1C and 5, respectively, were tested for anti-inflammatory activity in rats, using the standard rat foot edema test, according to the general procedure described by C. A. Winter et al., as first reported in the *Proceedings of the Society for Experimental Biology and Medicine*, Vol. 111, p. 544 (1962). The compounds were administered orally (by gavage) at 32 mg./kg. and the results obtained are reported below in terms of the percent (%) inhibition of edema formation afforded by each test compound as compared to the control (i.e., vehicle alone with no compound):

| Compound | % Inhibition at 32 mg./kg. |
| --- | --- |
| Product of Example 1B | 48 |
| Product of Example 1C | 16 |
| Product of Example 5 | 13 |

EXAMPLE 7

4-(2-Hydroxyethyl)-2-methyl-N-(2-pyridinyl)-2H-1,2-benzothiazine-3-carboxamide 1,1-dioxide, the final product of Example 1B, was tested for oral absorption potential according to the general procedure described by J. B. Dressman et al., as first reported in the *Journal of Pharmaceutical Sciences*, Vol. 74, No. 5, p. 588 (1985). The oral absorption potential test is used as a first approximation for predicting oral absorption of a given compound. It bears a strong relationship to the percentage of the drug absorbed. Values above 1.0 appear to correspond to virtually complete oral absorption, whereas values below this point indicate either a possible dose proportional absorption (e.g., 0-1.0) or poor oral absorption (e.g., <0).

In this connection, the prodrug final product of Example 1B and several commercial non-steroidal anti-inflammatory agents (NSAI) were first evaluated by high pressure liquid chromatography (RP-HPLC) to assign values for octanol-water partition coefficients and intrinsic water solubility. These values were then used to compute the oral absorption potential for each compound, either at a dose which was the molar equivalent to 20 mg. of piroxicam in the case of the prodrug or at the clinically-recommended (PDR) dose in the case of the commercial NSAI agents. The results obtained in this manner are summarized below in the following table, where the effect (water solubility and absorption potential) of the product of Example 1B is compared with that of other well-known anti-inflammatory agents, such as piroxicam, aspirin, indomethacin, ibuprofen and naproxen, respectively, at the various dose levels indicated:

| Compound | Oral Dose(mg.) | Water Solub.(mg/ml) | Absorption Potential |
|---|---|---|---|
| Prod. of Ex. 1B | 22.7 | 470 | 1.81 |
| Piroxicam | 20 | 26.5 | 1.11 |
| Aspirin | 325 | 1963 | 0.74 |
| Indomethacin | 25 | 0.7 | 0.65 |
| Ibuprofen | 400 | 0.3 | −0.86 |
| Naprofen | 250 | 8.1 | −0.06 |

From the data presented in this table, it is clear that the product of Example 1B has the highest oral absorption potential seen in the series of compounds tested, including even piroxicam when tested at an equivalent dose level. Moreover, the product of Example 1B exhibits this effect even though tested at a dose level that ranges well below ten percent of the dose level values of some the other NSAI agents tested.

We claim:

1. A compound of the formula:

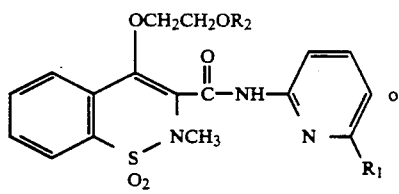

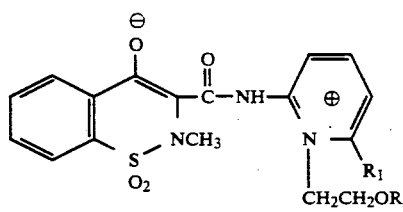

wherein $R_1$ is hydrogen, methyl, fluorine or chlorine, and $R_2$ is hydrogen.

2. A compound as claimed in claim 1 of the formula I.

3. A compound as claimed in claim 1 of the formula II.

4. A compound as claimed in claim 1 wherein $R_1$ is hydrogen.

5. A compound as claimed in claim 1 wherein $R_1$ is methyl.

6. A compound as claimed in claim 4 of the formula I.

7. A compound as claimed in claim 4 of the formula II.

8. A compound as claimed in claim 5 of the formula I.

9. A pharmaceutical composition comprising a pharmaceutically acceptable carrier and an effective anti-inflammatory amount of a compound as claimed in claim 1.

10. A method for treating inflammatory conditions in a warm-blooded animal, which comprises administering to said animal an effective anti-inflammatory amount of a compound as claimed in claim 1.

* * * * *